United States Patent [19]

Haugwitz et al.

[11] 4,076,828
[45] Feb. 28, 1978

[54] METHOD OF TREATING HELMINTHIASIS BY PARENTERAL ADMINISTRATION OF SULFOXIDE DERIVATIVES OF BENZIMIDAZOLES

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 769,632

[22] Filed: Feb. 17, 1977

[51] Int. Cl.² ........................................... A61K 31/415
[52] U.S. Cl. ................................................. 424/273 R
[58] Field of Search ......................................... 424/273

[56] References Cited

U.S. PATENT DOCUMENTS

| | | | |
|---|---|---|---|
| 3,574,845 | 4/1971 | Actor et al. | 424/273 |
| 3,928,375 | 12/1975 | Duwel et al. | 260/309.2 |
| 3,954,791 | 5/1976 | Loewe et al. | 424/273 |

Primary Examiner—Sam Rosen
Attorney, Agent, or Firm—Lawrence S. Levinson; Merle J. Smith; Burton Rodney

[57] ABSTRACT

A method is provided for treating or inhibiting helminthiasis by parenterally administering sulfoxide derivatives of benzimidazoles having the structure

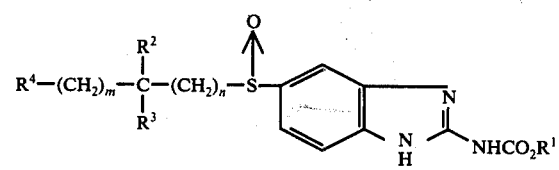

wherein $R^1$ is lower alkyl or phenyl-lower alkyl, $R^2$ and $R^3$ may be the same or different and are hydrogen or lower alkyl, $R^4$ is cycloalkyl, and $m$ is 0 to 3, $n$ is 0 to 3, $m + n$ being $\leq 5$. Pharmaceutical compositions for use in the above method are also provided.

16 Claims, No Drawings

METHOD OF TREATING HELMINTHIASIS BY PARENTERAL ADMINISTRATION OF SULFOXIDE DERIVATIVES OF BENZIMIDAZOLES

BACKGROUND OF THE INVENTION

Various benzimidazole compounds are known for their use as anthelmintic agents. For example, U.S. Pat. No. 3,574,845 to Actor et al and assigned to Smith Kline discloses 5(6)-benzene ring substituted benzimidazole-2-carbamate derivatives including 5(6)-methylthio-2-carboethoxyaminobenzimidazole and various 5(6) -alkyl-2-carbomethoxyaminobenzimidazoles.

U.S. Pat. Nos. 3,929,821 and 4,002,640 to Beard et al and assigned to Syntex disclose various 5(6)-benzene ring substituted benzimidazole-2-carbamate derivatives including 5(6) -alkylsulfinyl-2-carbomethoxyaminobenzimidazoles, as well as 5(6)-benzylsulfinyl-2-carbomethoxyaminobenzimidazole, 5(6)-phenylsulfinyl-2-carbomethoxyaminobenzimidazole, 5(6)-cycloalkylsulfinyl-2-carbomethoxyaminobenzimidazoles and 5(6)-cyclopropylmethylsulfinyl-2-carbomethoxyaminobenzimidazole.

The benzimidazoles mentioned above are said to be active orally.

Other benzimidazoles useful as anthelmintic agents are disclosed in U.S. Pat. Nos. 3,929,822, 3,929,823, 3,929,824, 3,935,209, 3,965,113 and 4,005,202 all to Beard et al and assigned to Syntex; U.S. Pat. Nos. 3,682,952 to Actor et al, 3,578,676 and 3,694,455 to Dunn, 3,915,986 and 3,969,526 to Gyurik, all assigned to Smith Kline; and U.S. Pat. No. 3,738,993 to Haugwitz et al assigned to Squibb.

The aforementioned patents teach that the benzimidazole compounds disclosed therein are useful orally in treating helminthiasis.

U.S. Pat. Nos. 3,954,791 to Loewe et al and 3,928,375 to Duwel et al, both assigned to Hoechst disclose 2-carbalkoxy-amino-benzimidazole-5(6)-phenyl and phenylthio ethers which are said to be active perorally and subcutaneously.

In accordance with the present invention, it is indeed surprising that 5(6) -alkylsulfinyl-2-carbomethoxyaminobenzimidazoles wherein the alkyl group includes a cycloalkyl substituent may be effectively administered parenterally in the treatment or prevention of helminthiasis inasmuch as most benzimidazole compounds are active only upon oral administration. Furthermore, this is especially surprising and unexpected in view of the above teachings in U.S. Pat. No. 3,574,845 to Actor et al which discloses that 5(6)-alkylthio-2-carboalkoxyaminobenzimidazoles and 5(6)-alkyl-2-carbomethoxyaminobenzimidazoles are useful perorally and the teachings in U.S. Pat. Nos. 3,929,821 and 4,002,640 to Beard et al which disclose that 5(6)-cyclopropylmethylsulfinyl-2-carbomethoxyaminobenzimidazole and the corresponding 5(6)-alkylsulfinyl-, 5(6)-cycloalkylsulfinyl-, 5(6)-benzylsulfinyl-, 5(6)-phenylsulfinyl-2- carbomethoxyaminobenzimidazoles are perorally active in the treatment of helminthiasis.

DESCRIPTION OF THE INVENTION

The present invention relates to a method for treating or inhibiting helminthiasis by parenterally administering to a mammalian host a sulfoxide derivative of a benzimidazole having the structure

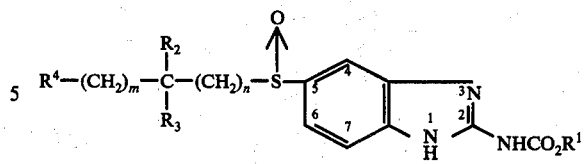

wherein $R^1$ is lower alkyl or phenyl-lower alkyl, $R^2$ and $R^3$ may be the same or different and are hydrogen or lower alkyl, and $R^4$ is cycloalkyl, $m$ is 0 to 3, $n$ is 0 to 3 and $m + n$ is $\leq 5$.

The term "lower alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like.

$(CH_2)_m$ and $(CH_2)_n$ represent a single bond or straight or branched chain alkylene radicals containing 3 or less carbons in the longest normal chain.

The term "phenyl lower alkyl" as used herein refers to lower alkyl groups as discussed above having a phenyl substituent, such as benzyl.

The term "cycloalkyl" includes cyclic hydrocarbon groups containing 3 to 12 carbons. Example of suitable cycloalkyl groups include cyclopropyl, cyclobutyl, cyclopentyl, cyclohexyl, cycloheptyl, cyclooctyl, cyclodecyl and cyclododecyl.

Preferred are those compounds wherein $R^1$ is methyl, ethyl, propyl or benzyl, $m$ is 0, $n$ is 0 or 1, $R^2$ is hydrogen or methyl, $R^3$ is hydrogen, $R^4$ is cyclopropyl, cyclopentyl, cyclohexyl, cyclooctyl.

Examples of compounds which may be employed in the method of the present invention include the following.

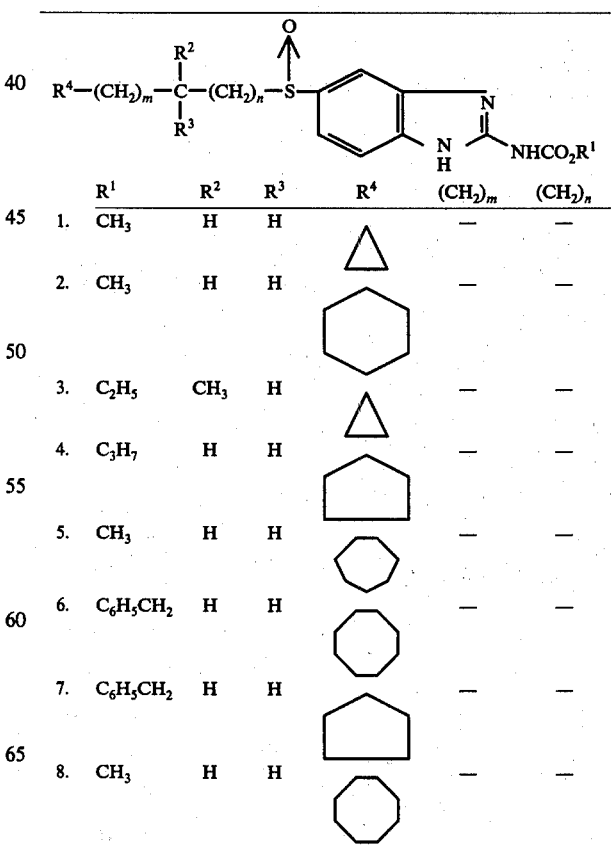

| | $R^1$ | $R^2$ | $R^3$ | $R^4$ | $(CH_2)_m$ | $(CH_2)_n$ |
|---|---|---|---|---|---|---|
| 1. | $CH_3$ | H | H | △ | — | — |
| 2. | $CH_3$ | H | H | ⬡ | — | — |
| 3. | $C_2H_5$ | $CH_3$ | H | △ | — | — |
| 4. | $C_3H_7$ | H | H | ⬠ | — | — |
| 5. | $CH_3$ | H | H | ⬡ | — | — |
| 6. | $C_6H_5CH_2$ | H | H | ⬡ | — | — |
| 7. | $C_6H_5CH_2$ | H | H | ⬠ | — | — |
| 8. | $CH_3$ | H | H | ⬡ | — | — |

-continued

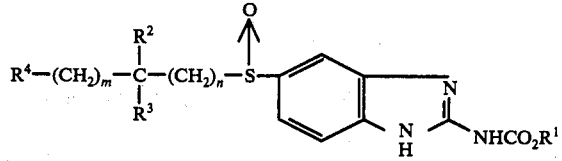

| | $R^1$ | $R^2$ | $R^3$ | $R^4$ | $(CH_2)_m$ | $(CH_2)_n$ |
|---|---|---|---|---|---|---|
| 9. | $CH_3$ | H | $C_2H_5$ | 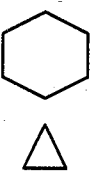 | $CH_2$ | — |
| 10. | $C_2H_5$ | H | H | △ | — | $CH_2$ |

The benzimidazole derivatives of structure I may be prepared by thiocyanation of o-nitroaniline to yield 4-thiocyano-2-nitroaniline (II). This product is then subjected to a sodium borohydride reduction to yield the corresponding 4-mercapto-2-nitroaniline (III). The mercapto derivative may be isolated or used directly for the next step. Thus, to the reaction mixture there is added the haloalkyl cycloalkane IV to furnish the sulfide V which preferably is converted to its acetyl derivative.

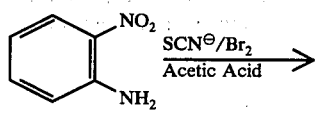

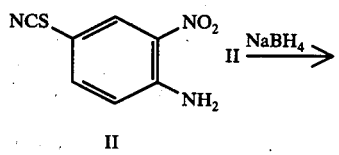

II

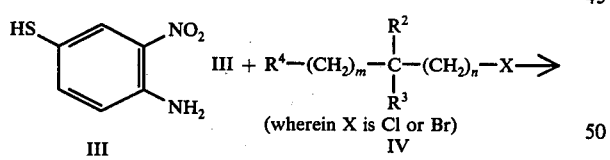

III

IV (wherein X is Cl or Br)

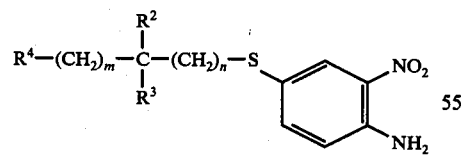

V

The sulfides of structure V (preferably their acetyl derivatives) are converted to the corresponding sulfoxides by oxidizing agent such as hydrogen peroxide, peracids (e.g., peracetic acid, m-chloroperbenzoic acid), manganese dioxide, sodium metaperiodate as outlined by Sandler and Caro (Organic Functional Group Preparations, 1968, p. 493).

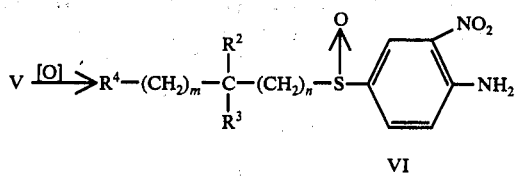

VI

The resulting sulfoxides VI may be purified by crystallization and then reduce to the corresponding o-phenylene diamine VII. Either chemical or catalytic reduction may be used. For the chemical reduction the procedure outlined by Sandler and Caro (Organic Functional Group Preparations, 1968, pp. 339–340) is preferred. The final step in the synthesis of I, namely ring closure of VII to furnish I, can be achieved in various ways. Whereas refluxing of VII with the isolated thiourea derivative VIII in alcohols such as methanol or ethanol will furnish I, the preferred method of preparing I is by forming VIII in situ and then without isolating it adding VII and refluxing it for 30 minutes to 5 hours to yield the desired product.

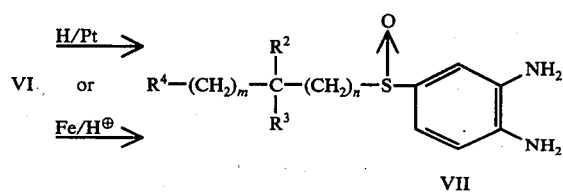

VII

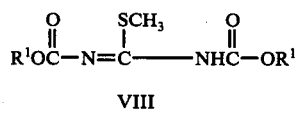

VIII

An alternative route toward the intermediate VII offers the reaction of IX with the requisite mercaptoalkyl cycloalkane X to yield XI. Here, in contrast to the alkylation step described above, (i.e., III → V) the reaction temperature has to be higher and the reaction periods have to be longer. Oxidation of XI yields the sulfoxide XII which on reduction furnishes the diamine VII.

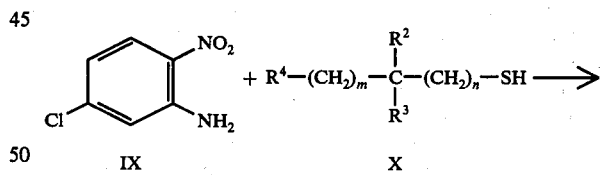

IX                X

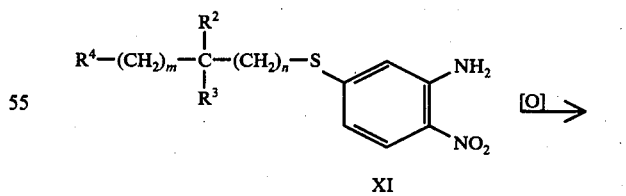

XI

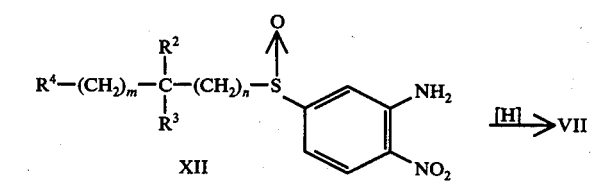

XII

Compounds of structure I may also by synthesized by converting intermediate V into the o-phenylenediamine XIII as outlined above which is then cyclized to the benzimidazole XIV. The final step, i.e., oxidation of XIV, yields I.
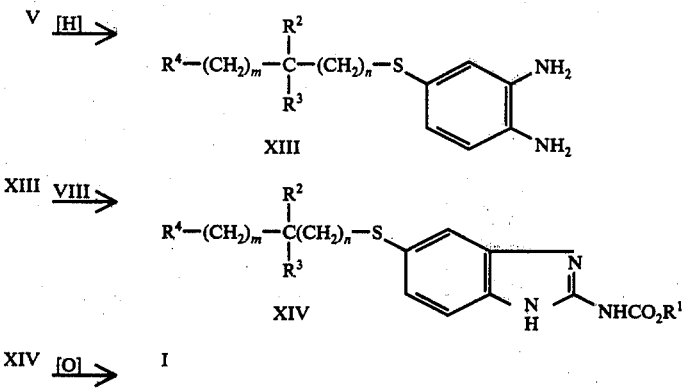
Examples of suitable haloalkyl cycloalkanes of formula IV suitable for use herein include the following.

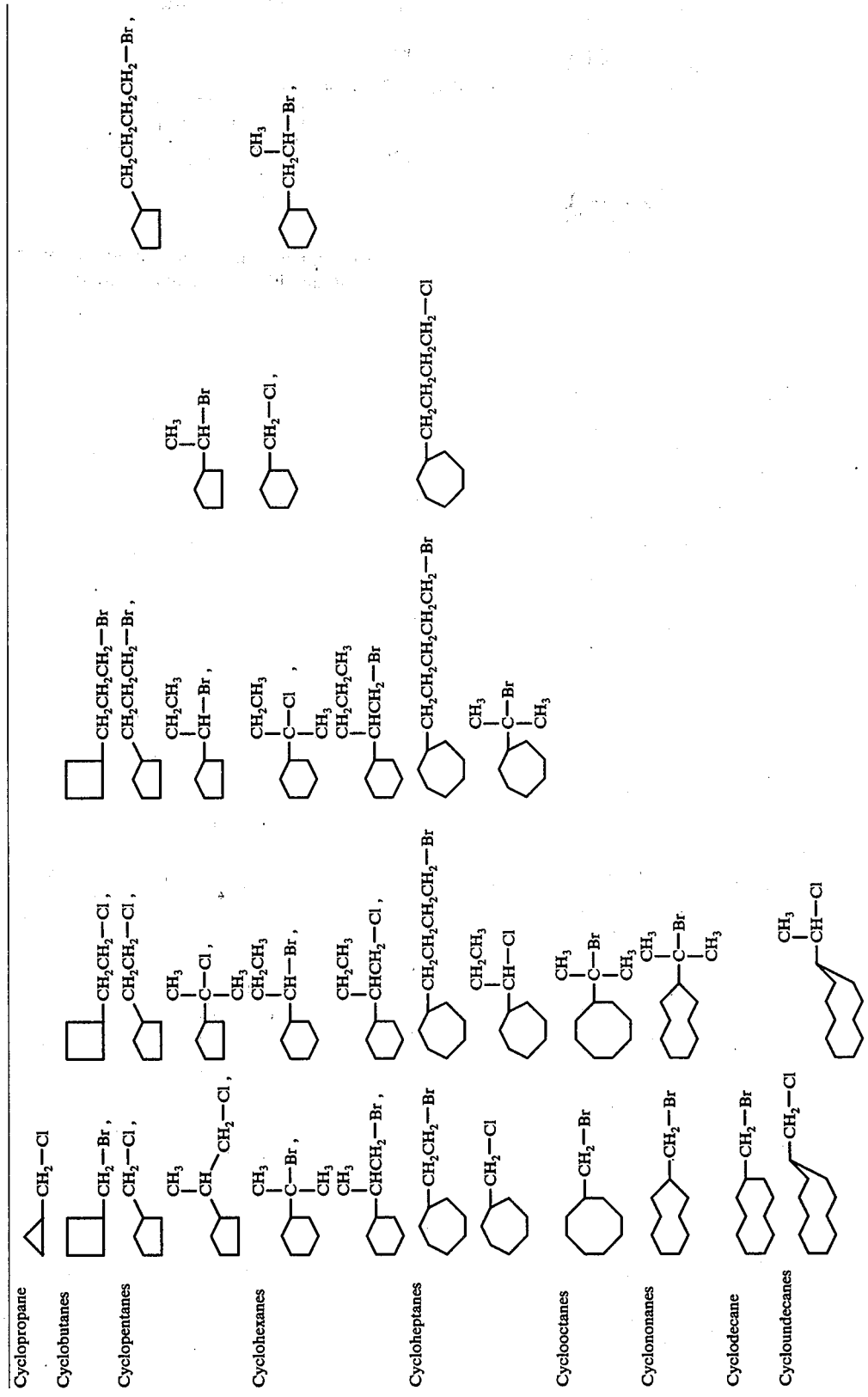

A great variety of haloalkyl cycloalkanes IV are commercially available. In some cases the requisite haloalkyl cycloalkane has to be synthesized, for example, from the corresponding alcohols by standard reactions.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

In accordance with the present invention, the compounds of formula I are administered parenterally, such as subcutaneously, intravenously, intramuscularly or interperitoneally to a mammalain host in the treatment and/or prevention of helminthiasis. Helminthiasis is a parasitic disease which causes widespread and ofter serious infection in domesticated animals such as swine, horses, cattle, dogs, cats and sheep. The compounds administered parenterally are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia and liver flukes. In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil:benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 0.2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., (Tweens)] and fatty acid monoglycerides or diglycerides. Other surfactants suitable for use herein are disclosed in the published literature, for example, Kirk-Othmer, Encyclopedia of Chemical Technology, Second Edition, Volume 19, pages 507 et seq.

In general, in carrying out the method of the invention, the parenteral composition described above will be administered to animals in a single dose to provide from about 1 to about 100 mg active compound per kilogram of animal body weight. It is preferred to employ in the range of 2.5–25 mg per kilogram of body weight. The compounds may be divided into a plurality of smaller doses given over one or more days, for example, up to 14 days.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

Parenteral Composition Containing [5-[(Cyclopropylmethyl)sulfinyl]-1H-benzimidazol-2-yl]carbamic acid, methyl ester A. 4(Cyclopropylmethyl)thio-2-nitroaniline To a stirred mixture of 11.7 g (0.06 mole) of 2-nitro-4-thiocyanoaniline in 500 ml of absolute ethanol under nitrogen there is added 2.5 g (0.06 mole) of sodium borohydride in portions. The mixture is stirred at room temperature for 15 minutes and then refluxed for 15 minutes. The heating mantle is removed and 3.9 g (0.06 mole) of KOH in 25 ml of absolute ethanol is added. THe mixture is stirred for 1 minute. A solution of 4.8 g (0.06 mole) of (chloromethyl)cyclopropane in 10 ml of absolute ethanol is added and the mixture is stirred at room temperature for 15 minutes then refluxed for 2 hours. Equal amounts of water and $CHCl_3$ are added until 2 layers are formed. The organic layer is separated, dried ($MgSO_4$), and the solvent removed in vacuo to give 9.1 g of an orange-red solid, m.p. 45°–47°.

B. 4-(Cyclopropylmethyl)thio-o-phenylenediamine

A mixture of 6.75 g (0.03 mole) of 4-(cyclopropylmethyl)thio-2-nitroaniline and 0.5 g of $PtO_2$ in 200 ml of absolute ethanol is reduced on the Parr hydrogenator at 50 psi. The mixture is filtered and the solvent in removed in vacuo to yield the solid diamine, m.p. 57°–60° C.

C.

[5-[(Cyclopropylmethyl)thio]-1H-benzimidazol-2-yl]carbamic acid, methyl ester

To a mixture of 9 g of 2-methyl-2-thiopseudourea sulfate in 6 ml of water there is added 5.7 ml of methyl chloroformate at 0° C and the mixture is stirred for 15 minutes. Then there is added 12 ml of 25% NaOH dropwise and the mixture is stirred for 15 minutes. Then there is added 6 ml of acetic acid dropwise and the mixture is stirred for 15 minutes. The total amount of 4-(cyclopropylmethyl)thio-o-phenylenediamine from above in 50 ml of methanol is then added and the mixture is refluxed for 2 hours. The alcohol is removed in vacuo and water is added. The resulting solid is filtered off and crystallized from glyme-acetonitrile to yield 3.9 g, m.p. 228°–231°.

D.

[5-[(Cyclopropylmethyl)sulfinyl]-1H-benzimidazol-2-yl]carbamic acid, methyl ester To a solution of 2.77 g of [5-[(cyclopropylmethyl)thio]-1H-benzimidazol-2l -yl]carbamic acid, methyl ester in 120 ml of chloroform and 120 ml of acetic acid at −20°, there is added at once a solution of 2.1 g of m-chloroperbenzoic acid in 20 ml of chloroform. The stirred mixture is allowed to react slowly at room temperature after 4 hours of stirring. The chloroform is evaporated in vacuo. The remaining mixture is neutralized with aqueous sodium bicarbonate. The resulting solid is filtered off and crystallized from glyme to yield 1.2 g, m.p. 223°-224° of the title compound.

E. Parenteral Formulation of [5-[(Cyclopropylmethyl)sulfinyl]-1H-benzimidazol-2-yl]carbamic acid, methyl ester A suspension suitable for subcutaneous administration is prepared by dispersing 150 mg of [5-[(cyclopropylmethyl)sulfinyl]-1H-benzimidazol-2-yl]carbamic acid, methyl ester in about 10 ml of water for injection, USP. The resulting suspension contains 1.5% by weight of the benzimidazole compound.

EXAMPLE 2

Testing of Parenteral Formulation of [5-[(Cyclopropylmethyl)sulfinyl]-1H-benzimidazol-2-yl]carbamic acid, methyl ester The following test is carried out to determine the effectiveness of treating sheep infected with adult and immature lung worm and tapeworm by subcutaneously administering a single dose of an aqueous suspension of [5-[(cyclopropylmethyl)sulfinyl]-1H-benzimidazol-2-yl]carbamic acid, methyl ester (hereinafter referred to as "benzimidazole compound") prepared in Example 1 so as to inject 20 mg of the "benzimidazole compound" per kg of body weight of the test animal.

Egg per gram of feces (EPG) counts are conducted 2-4 days (avg. 3) prior to subcutaneously administering the "benzimidazole compound" in order to determine the degree of parasitism of the test animal. Generally, animals are used which have at least 10,000 eggs per gram of feces although, on occasion, lambs with 8-9,000 eggs per gram can be used. An average pretreatment EPG is calculated for the test animal and medication is given according to individual body weights (20 mg/kg).

EPG's are conducted daily during the week the animal is on test and the final three (3) EPG's are used to calculate an average post-treatment EPG. The percent reduction in the EPG count for a given compound is calculated by taking the average pretreatment EPG and dividing this figure into the average post-treatment EPG and subtracting the quotient from 100.

Results of EPG determination using sheep following subcutaneous treatment with "benzimidazole compound"

| PRETREATMENT EPG | |
|---|---|
| Unmedicated Control | Benzimidazole Compound |
| 10,800 | 14,200 |
| 25,600 | 16,200 |
| 29,800 | 11,100 |
| 66,200÷3 | 41,500÷3 |
| Avg. 22,067 | 13,833 |

| POST-TREATMENT EPG | |
|---|---|
| Unmedicated Control | Benzimidazole Compound |
| 41,400 | 0 |
| 34,600 | 200 |
| 21,600 | 200 |
| 97,600÷3 | 400÷3 |
| Avg. 32,533 | 133 |
| 0% reduction in EPG | 99.99% reduction in EPG |

The "benzimidazole compound" in the form of an aqueous suspension reduces the fecal egg count (EPG) by 100% when administered subcutaneously at 20 mg/kg.

Similar tests are carried out using different dosages of the aqueous suspension of the "benzimidazole compound," namely, 10 mg/kg, 5 mg/kg and 2.5 mg/kg, administered subcutaneously. The results of these tests show that fecal egg count (EPG) is reduced by 100% at 10 mg/kg, 100% at 5 mg/kg and 94% at 2.5 mg/kg.

EXAMPLE 3

Parenteral Composition Containing [5-[(Cyclohexylmethyl)sulfinyl]-1H-benzimidazol-2-yl]carbamic acid, methyl ester A. 2-Nitro-4-thiocyanoaniline To a well-stirred mixture of 108 g of o-nitroaniline and 128 g of ammonium thiocyanate in 400 ml of acetic acid there is added dropwise a solution of 128 g of bromine in 160 ml of acetic acid below 20° C. The mixture is stirred for 4 hours at room temperature and then poured into 4 liters of water. The resulting solid is filtered off and crystallized from ethanol to yield 86.7 g, m.p. 111°-114° C.

B. 4-(Cyclohexylmethyl)thio-2-nitroaniline

To a stirred mixture of 9.75 g (0.05 mole) of 2-nitro-4-thiocyanoaniline in 500 ml of absolute ethanol under nitrogen there is added 2.04 g (0.05 mole) of sodium borohydride in portions. The mixture is stirred at room temperature for 15 minutes and then refluxed for 15 minutes. The heating mantle is removed and 3.25 g (0.05 mole) of KOH in 15 ml of absolute ethanol is added. The mixture is stirred for 1 minute. A solution of 8.85 g (0.05 mole) of cyclohexylmethyl bromide in 15 ml of absolute ethanol is added and the mixture is stirred at room temperature for 15 minutes then refluxed for 1 hour. Equal amounts of water and $CHCl_3$ are added until 2 layers are formed. The organic layer is separated, dried ($MgSO_4$) and the solvent removed in vacuo. The residue is crystallized from ethyl ether to yield 8.3 g, m.p. 80°-82°.

C. 4-(Cyclohexylmethyl)thio-o-phenylenediamine

A mixture of 8.0 g (0.03 mole) of 4-(cyclohexylmethyl)thio-2-nitroaniline and 0.5 g of $PtO_2$ in 200 ml of absolute ethanol is reduced on the Parr hydrogenator at 50 psi until the theoretical amount of $H_2$ is absorbed. The mixture is filtered and the solvent is removed in vacuo to yield the solid diamine, m.p. 76°-79° C.

D.

[5-[(Cyclohexylmethyl)thio]-1H-benzimidazol-2-yl]carbamic acid, methyl ester

To a mixture of 9 g of 2-methyl-2-thiopseudourea sulfate in 6 ml of water there is added 5.7 ml of methyl chloroformate at 0° C and the mixture is stirred for 15 minutes. Then there is added 12 ml of 25% NaOH dropwise and the mixture is stirred for 15 minutes. Then the total amount of 4-(cyclohexylmethyl)thio-o-phenylenediamine from the above reaction in 50 ml of methanol is added and the mixture is refluxed for 2 hours. The alcohol is removed in vacuo and water is added. The resulting solid is filtered off and crystallized from $CH_3CN$ to yield 2.5 g, m.p. 200°-204° C.

E.

[5-[(Cyclohexylmethyl)sulfinyl]-1H-benzimidazol-2-yl]carbamic acid, methyl ester To a mixture of 3.2 g of [5-[(cyclohexylmethyl)thio]-1H-benzimidazol-2-yl]carbamic acid, methyl ester in 120 ml $CHCl_3$ and 120 ml HOAc at −20° C there is added a solution of 2.1 g of m-chloroperbenzoic acid. The resulting mixture is allowed to warm to room temperature. Stirring is continued for 5 hours and then CHCl₃ is removed in vacuo. Water is added and the solution is neutralized with NaHCO₃. The resulting solid is filtered off and crystallized from acetonitrile (1.5 g) to give the title compound, m.p. 272°–274° C.

F. Parenteral Formulation of [5-[(Cyclohexylmethyl)sulfinyl]-1H-benzimidazol-2-yl]carbamic acid, methyl ester A suspension suitable for subcutaneous administration is prepared by dispersing 300 mg of [5-[(cyclohexylmethyl)sulfinyl]-1H-benzimidazol-2-yl]carbamic acid, methyl ester and 100 mg carboxymethyl cellulose in about 10 ml of water for injection, USP. The resulting suspension contains 3% by weight of the benzimidazole compound.

EXAMPLE 4

Parenteral Composition Containing [5-[(Cyclobutylmethyl)sulfinyl]-1H-benzimidazol-2-yl]carbamic acid, methyl ester A. [5-[(Cyclobutylmethyl)thio]-1H-benzimidazol-2-yl]-carbamic acid, methyl ester To a solution of 15 g (0.174 mole) cyclobutanemethanol and 26.4 g triethylamine (0.192 mole, 1.5 equivalent) in 800 ml methylene chloride at 0° C is added 14.8 ml (1.1 equivalent) methanesulfonyl chloride in 25 ml methylene chloride over 1 hour. The solution is stirred for an additional 0.5 hour, then washed successively with cold 10% HCl, ice-water, concentrated aqueous NaHCO₃, and aqueous NaCl. The organic layer is dried, filtered and stripped to yield 27.8 g of cyclobutanemethyl mesylate as a water-white liquid.

To a stirred solution of 12.3 g (0.063 mole) 2-nitro-4-thiacyanoaniline in 600 ml EtOH, is added 2.84 g NaBH₄, all at once. The mixture is stirred for 45 minutes and 4.95 g KOH pellets and 10.35 g (0.063 mol) cyclobutanemethyl mesylate are added. The resulting mixture is heated to reflux for 10 minutes, and stirred at room temperature overnight. The mixture is partitioned between water and methylene chloride; the organic layer is separated, dried, filtered and stirred to yield 15 g, red crystalline solid which is recrystallized from ether-petroleum ether to yield 11.6 g of 4-(cyclobutylmethylthio)-2-nitroaniline as a red crystalline solid, m.p. 49°–53°.

11 g of the above nitro-aniline is reduced under pressure in 200 ml absolute ethanol with 1.1 g PtO₂. The solution is filtered and stripped to yield 9.7 g of 4-(cyclobutylmethylthio)-o-phenylenediamine as a dark solid.

9.2 g 2-methyl-2-thiopseudo-urea is added to 9.09 ml water at 0° C. To this is added 8.63 ml methyl chloroformate; the resulting paste is stirred 15 minutes. 18.18 ml of 25% aqueous NaOH is added dropwise and then stirred for 15 minutes. 9.09 ml glacial acetic acid is added dropwise and stirred for 15 minutes. To this mixture is added 9.45 g (0.045 mole) of the above phenylene diamine in 25 ml methanol, and the resulting mixture heated to reflux for 3 hours, cooled, and the product filtered. The resulting solid is washed with ether and acetonitrile and dried to yield 9.4 g of a purple solid. The above solid is recrystallized from glyme to yield 5.6 g of [5-[(cyclobutylmethyl)thio-1H-benzimidazol-2-yl)carbamic acid, methyl ester as a tan powder, m.p. 216°–218°.

B. [5-[(Cyclobutylmethyl)sulfinyl]-1H-benzimidazol-2-yl]carbamic acid, methyl ester 2.5 g (0.0086 mole) of the [5-[(cyclobutylmethyl)thio-1H-benzimidazol-2-yl]carbamic acid, methyl ester is dissolved in 60 ml acetic acid and 60 ml chloroform. To this is added 1.5 g (1 equivalent at 100%) m-chloroperbenzoic acid at −10° C over 0.5 hour. The mixture is stirred while temperature rises to room temperature.

The chloroform is stripped, and acetic acid azeotroped with heptane yielding an amber oil, which is digested with aqueous NaHCO₃; the resulting solids are filtered, washed with H₂O, dried overnight and recrystallized from glyme to yield 1.1 g of the title compound, m.p. 198°–206°.

C. Parenteral Formulation of [5-[(Cyclobutylmethyl)sulfinyl]-1H-benzimidazol-2-yl]carbamic acid, methyl ester A suspension suitable for subcutaneous administration is prepared by dispersing 300 mg of [5-[(cyclobutylmethyl)sulfinyl]-1H-benzimidazol-2-yl]carbamic acid, methyl ester in about 10 ml of water for injection, USP. The resulting suspension contains 3% by weight of the benzimidazole compound.

EXAMPLE 5

Parenteral Composition Containing [5-[(Cyclopropylmethyl)sulfinyl]-1H-benzimidazol-2-yl]carbamic acid, benzyl ester A. Following the procedure of Example 1 and substituting benzyl chloroformate for methyl chloroformate, the above benzimidazole compound is obtained.

B. Parenteral Formulation of [5-[(Cyclopropylmethyl)sulfinyl]-1H-benzimidazol-2-yl]carbamic acid, benzyl ester A suspension suitable for subcutaneous administration is prepared by dispersing 300 mg of [5-[(cyclopropylmethyl)sulfinyl]-1H-benzimidazol-2-yl]carbamic acid, benzyl ester and 100 mg of carboxymethyl cellulose in about 10 ml of water for injection, USP. The resulting suspension contains 3% by weight of the benzimidazole compound.

EXAMPLES 6 to 13

A. Following the procedure of Example 3 except substituting for cyclohexylmethyl bromide the compound shown in column I of Table I below and substituting for methyl chloroformate the compound shown in column II, the product shown in column III is obtained.

TABLE I $$R^4-(CH_2)_m-\underset{R^3}{\overset{R^2}{C}}-(CH_2)_n-X \qquad HCOOR^1 \qquad R^4-(CH_2)_m-\underset{R^3}{\overset{R^2}{C}}-(CH_2)_n-\overset{\overset{O}{\uparrow}}{S}\text{-benzimidazolyl-NHCO}_2R^1$$

| Ex. No. | $R^4$ | $-(CH_2)_m-\underset{R^3}{\overset{R^2}{C}}-(CH_2)_n-$ | X | $R^1$ | $R^4-(CH_2)_m-\underset{R^3}{\overset{R^2}{C}}-(CH_2)_m$ | $R^1$ |
|---|---|---|---|---|---|---|
| 6. | cyclopropyl | $-\underset{\phantom{x}}{\overset{CH_2CH_3}{CH}}-$ | Cl | n-$C_3H_7$ | as in Column I | as in Column II |
| 7. | cyclopentyl | $-\underset{\phantom{x}}{\overset{C_2H_5}{CH}}-$ | Br | $C_2H_5$ | | |
| 8. | cycloheptyl | $-\underset{CH_3}{\overset{CH_3}{C}}-$ | Cl | $CH_3$ | | |
| 9. | cyclohexyl | $-(CH_2)_2-$ | Br | $C_3H_7$ | | |
| 10. | $C_{12}$ | $-CH_2-$ | Br | $C_2H_5$ | | |
| 11. | cycloheptyl | $-(CH_2)_2-$ | Cl | n-$C_4H_9$ | | |
| 12. | $C_{11}$ | $-\underset{\phantom{x}}{\overset{CH_3}{CH}}-$ | Cl | $CH_3$ | | |
| 13. | $C_{12}$ | $-CH_2-$ | Br | $CH_3$ | | |

B. Parenteral Formulations of Benzimidazole Compounds of Examples 6 to 13

Suspensions suitable for subcutaneous administration are prepared by dispersing 300 mg of a benzimidazole compound of Examples 6 to 13 in about 10 ml of water for injection, USP. The resulting suspensions contain 3% by weight of the benzimidazole compounds.

What is claimed is:

1. A method of treating or preventing helminthiasis, which comprises parenterally administering to a mammalian host an effective amount of a compound of the structure

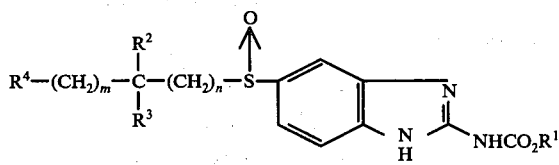

wherein $R^1$ is lower alkyl, phenyl-lower alkyl, $R^2$ and $R^3$ are the same or different and are selected from the group consisting of hydrogen or lower alkyl, and $R^4$ is cycloalkyl, m is 0 to 3, n is 0 to 3 and m + n is $\leq$ 5, dispersed in a non-toxic nonpyrogenic physiologically acceptable carrier.

2. The method as defined in claim 1 where in said compound $R^1$ is lower alkyl or benzyl.

3. The method as defined in claim 1 where in said compound $R^2$ and $R^3$ are hydrogen or methyl.

4. The method as defined in claim 1 wherein in said compound $R^4$ contains 3 to 12 carbons.

5. The method as defined in claim 1 where in said compound m is 0 and n is 0, and $R^2$ and $R^3$ are hydrogen.

6. The method as defined in claim 1 wherein said compound has the name [5-[(cyclopropylmethyl)sulfinyl]-1H-benzimidazol-2-yl]carbamic acid, methyl ester.

7. The method as defined in claim 1 wherein said compound has the name [5-[(cyclobutylmethyl)sulfinyl]-1H-benzimidazol-2-yl]carbamic acid, methyl ester.

8. The method as defined in claim 1 wherein said compound has the name [5-[(cyclohexylmethyl)sulfinyl]-1H-benzimidazol-2-yl]carbamic acid, methyl ester.

9. The method as defined in claim 1 wherein said compound is administered subcutaneously.

10. The method as defined in claim 1 wherein said compound is administered intravenously.

11. An injectable composition for use in treating or preventing helminthiasis in mammalian species comprising an effective amount of a compound of the structure

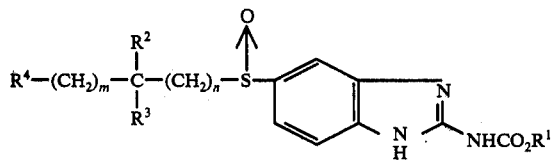

wherein $R^1$ is lower alkyl, phenyl-lower alkyl, $R^2$ and $R^3$ are the same or different and are selected from the group consisting of hydrogen or lower alkyl, and $R^4$ is cycloalkyl, $m$ is 0 to 3, $n$ is 0 to 3 and $m + n$ is $\leq$ 5, and a non-toxic non-pyrogenic physiologically acceptable carrier therefor selected from the group consisting of benzyl benzoate, 1,3-butylene glycol, ethyl oleate, glyceryl triacetate, mixtures thereof and a mixture of benzyl benzoate and sesame oil.

12. The composition as defined in claim 11 wherein said compound has the name [5-[(cyclopropylmethyl)-sulfinyl]-1H-benzimidazol-2-yl]carbamic acid, methyl ester.

13. An injectable composition for use in treating or preventing helminthiasis in mammalian species comprising an effective amount of a compound of the structure

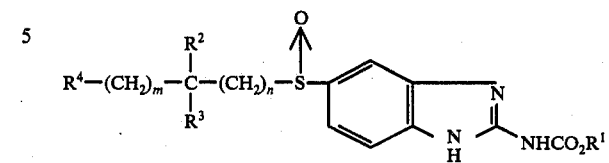

wherein $R^1$ is lower alkyl, phenyl-lower alkyl, $R^2$ and $R^3$ are the same or different and are selected from the group consisting of hydrogen or lower alkyl, and $R^4$ is cycloalkyl, $m$ is 0 to 3, $n$ is 0 to 3 and $m + n$ is $\leq$ 5, and physiologically acceptable salts thereof, and sterile water for injection USP as a carrier therefor.

14. The composition as defined in claim 13 wherein said compound has the name [5-[(cyclopropylmethyl)-sulfinyl]-1H-benzimidazol-2-yl]carbamic acid, methyl ester.

15. The composition as defined in claim 13 further including a non-toxic physiologically acceptable suspending agent.

16. The composition as defined in claim 15 wherein said suspending agent is carboxymethyl cellulose.

* * * * *

UNITED STATES PATENT OFFICE
CERTIFICATE OF CORRECTION

Patent No. 4,076,828                                Dated February 28, 1978

Inventor(s) Rudiger D. Haugwitz et al.

It is certified that error appears in the above-identified patent and that said Letters Patent are hereby corrected as shown below:

Column 3, line 63, "agent" should read --agents--.
Column 4, line 11, "reduce" should read --reduced--.
Column 10, line 39, "in" should read --is--.
Column 10, line 64, "21-yl" should read --2-yl--.
Column 13, line 49, "stirred" should read --stripped--.
Columns 15 and 16, Table I, the column headings should read

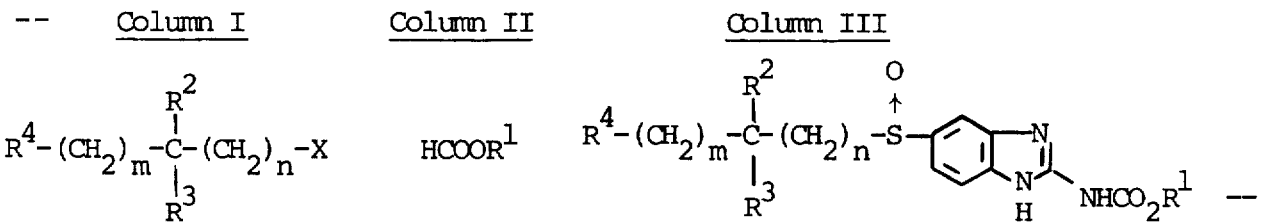

Column 16, line 43, "nonpyrogenic" should read --non-pyrogenic--.

Signed and Sealed this

Twentieth Day of June 1978

[SEAL]

Attest:

RUTH C. MASON
Attesting Officer

DONALD W. BANNER
Commissioner of Patents and Trademarks